(12) United States Patent
Reiss

(10) Patent No.: US 8,463,381 B2
(45) Date of Patent: Jun. 11, 2013

(54) METHODS AND DEVICES FOR RESPONDING TO PREMATURE VENTRICULAR CONTRACTIONS WHILE IN AAI(R) MODE

(75) Inventor: Joshua Reiss, Kirkland, WA (US)

(73) Assignee: Pacesetter, Inc., Sunnyvale, CA (US)

( * ) Notice: Subject to any disclaimer, the term of this patent is extended or adjusted under 35 U.S.C. 154(b) by 1171 days.

(21) Appl. No.: 12/268,292

(22) Filed: Nov. 10, 2008

(65) Prior Publication Data

US 2010/0010554 A1    Jan. 14, 2010

Related U.S. Application Data

(60) Provisional application No. 61/080,566, filed on Jul. 14, 2008.

(51) Int. Cl.
*A61N 1/00* (2006.01)

(52) U.S. Cl.
USPC ................................. 607/17; 607/9

(58) Field of Classification Search
USPC ................................. 607/9, 14, 17
See application file for complete search history.

(56) References Cited

U.S. PATENT DOCUMENTS

| | | | |
|---|---|---|---|
| 5,097,832 A | 3/1992 | Buchanan | |
| 5,318,594 A | 6/1994 | Limousin et al. | |
| 5,417,714 A | 5/1995 | Levine et al. | |
| 5,514,164 A | 5/1996 | Mann et al. | |
| 6,122,546 A | 9/2000 | Sholder et al. | |
| 6,496,730 B1 * | 12/2002 | Kleckner et al. | 607/9 |
| 6,584,354 B1 | 6/2003 | Mann et al. | |
| 6,662,049 B1 | 12/2003 | Miller | |
| 6,772,005 B2 | 8/2004 | Casavant et al. | |
| 7,130,683 B2 | 10/2006 | Casavant et al. | |
| 7,130,685 B2 | 10/2006 | Casavant et al. | |
| 7,164,946 B2 | 1/2007 | Amblard et al. | |
| 7,184,834 B1 | 2/2007 | Levine | |
| 7,218,965 B2 | 5/2007 | Casavant et al. | |
| 7,254,441 B2 | 8/2007 | Stroebel | |
| 7,333,856 B1 | 2/2008 | Er et al. | |
| 2004/0034390 A1 * | 2/2004 | Casavant et al. | 607/9 |
| 2007/0060963 A1 | 3/2007 | Casavant et al. | |

OTHER PUBLICATIONS

Gillis et al, "Reducing Unnecessary Right Ventricular Pacing with the Managed Ventricular Pacing (MVP) Mode in Patients with Sinus Node Disease and AV Block", Pacing Clin Electrophysiol. 2006;29(7):697-705.

(Continued)

*Primary Examiner* — Christopher D Koharski
*Assistant Examiner* — Catherine Voorhees
(74) *Attorney, Agent, or Firm* — Steven M. Mitchell

(57) ABSTRACT

While a cardiac device is in AAI(R) mode, a ventricular channel is monitored for a premature ventricular contraction (PVC). In response to detecting a PVC while the device is in AAI(R) mode, a refractory period is started in an atrial channel to prevent a retrograde atrial event that may occur due to the PVC from resetting an atrial escape interval (AEI). Additionally, during such a relative refractory period in the atrial channel, the atrial channel is monitored for a retrograde atrial event that may occur due to the PVC. If a retrograde atrial event is detected, then the refractory period in the atrial channel is terminated, and an antegrade conduction restoration interval (ACRI) is started. The ACRI is a programmed period that specifies how long to wait after a retrograde atrial event is detected before pacing the atrium.

21 Claims, 7 Drawing Sheets

OTHER PUBLICATIONS

"MVP Promotes Intrinsic Conduction," © 2008 Medtronic, Inc., http://www.medtronic.com/physician/brady/enrhythm/mvp.html.
Ellenbogen, "Minimizing Right Ventricular Pacing with a New Pacing Algorithm for Implantable Pacemakers and Defibrillators: ADI Mode," EP Lab Digest, vol. 6 Publication Date: Mar. 1, 2006, available at http://www.eplabdigest.com/articles/Minimizing-Right-Ventricular-Pacing-with-a-New-Pacing-Algorithm-Implantable-Pacemakers-and-.

* cited by examiner

METHODS AND DEVICES FOR RESPONDING TO PREMATURE VENTRICULAR CONTRACTIONS WHILE IN AAI(R) MODE

PRIORITY CLAIM

This application claims priority under 35 U.S.C. §119(e) to U.S. Provisional Patent Application No. 61/080,566, filed on Jul. 14, 2008, which is incorporated herein by reference.

FIELD OF THE INVENTION

Embodiments of the present invention generally relate to implantable dual chamber pacemakers that mode switch between different pacing modes. Specific embodiments relate to dual chamber pacemakers that mode switch between MI(R) and DDD(R) pacing modes in a manner that preferably suppresses ventricular pacing when possible.

BACKGROUND

The DDD(R) pacing mode is often used in patients with Sick Sinus Syndrome (SSS), a term that covers a large array of sinus node disease states. Such patients often have intact AV conduction. If the pacemaker's AV interval (also known as AV delay) is not properly programmed, the pacemaker will deliver an unneeded and undesirable ventricular pacing pulse. More specifically, in the DDD(R) pacing mode, the ventricular sensing channel waits for a conducted beat until the programmed AV interval (AV delay) times out. If an intrinsic ventricular activation is not detected during the programmed AV delay, ventricular pacing is performed. In certain patients, this may result in a higher than necessary percentage of ventricular pacing.

There is growing medical evidence that inappropriate ventricular pacing has disadvantageous short-term hemodynamic effects and may prove harmful when allowed to continue for an extended period of time. For example, studies have shown that ventricular pacing results in asynchronous delayed activation of the ventricular tissue, which compromises hemodynamics in mammals. Canine studies have shown that right ventricular apical (RVA) pacing causes a negative inotropic effect and an undesirable reduction in cardiac efficiency. Additionally, long term RVA pacing has been shown to lead to permanent changes including myofibrillar cellular disarray, myocardial perfusion defects, and structural abnormalities. Each of these may further contribute to deterioration of left ventricular function.

Further studies have suggested that high rate ventricular pacing renders patients more susceptible to the induction of ventricular tachycardia, as compared to high rate atrial pacing with normal ventricular contractions. Such studies, combined with the growing body of evidence showing the detrimental effects of long-term ventricular pacing, has led to more deliberate efforts by clinicians and implantable cardiac device manufacturers to allow for normal ventricular activation when programming dual chamber bradycardia devices.

To reduce the extent of ventricular pacing, medical device manufacturer Medtronic has developed an algorithm that it calls "Managed Ventricular Pacing" (MVP), which is believed to have been implemented in both implantable defibrillators and pacemakers. In U.S. Pat. No. 7,130,683, entitled "Preferred ADI/R: A Permanent Pacing Mode to Eliminate Ventricular Pacing While Maintaining Back Support", which is assigned to Medtronic, the MVP acronym equivalently stands for "Minimum Ventricular Pacing". The MVP algorithm, which is described in some detail below, is described in more detail in U.S. Pat. No. 7,130,683, which is incorporated herein by reference.

In the MVP algorithm, the AAI(R) mode is the primary mode of pacing. In the AAI(R) mode, sensing occurs in the atrium, pacing occurs in the atrium, and atrial pacing is inhibited if an intrinsic atrial event (i.e., a P wave) is detected within a programmed atrial escape interval (AEI). However, unlike a typical AAI(R) mode of operation, in the MVP algorithm ventricular events are also sensed (i.e., the ventricular channel is monitored), and thus this mode may alternatively be referred to as an ADI(R) mode, or AAI(R)+mode, because there is ventricular backup. So long as a ventricular event is sensed anywhere within a given A-A interval, the pacing mode remains in the MI(R) mode. However, ventricular backup pacing occurs as needed, in the presence of a transient loss of AV conduction. More specifically, when a P wave is blocked (i.e., not conducted through the AV node), resulting in an atrial event not being sensed within the A-A interval, a single ventricular pace is provided, which can be synchronized on the next P wave.

When there is persistent loss of AV conduction, the pacing mode is switched to the DDD(R) mode. For example, if there is loss of AV conduction for 2 out of 4 pacing cycles (e.g., 2 out of 4 A-A intervals), the algorithm performs a mode-switch to the DDD(R) mode. Pacing occurs in the DDD(R) mode for a period of time (e.g., 1 minute), after which the algorithm checks for the resumption of intact conduction, e.g., by switching to the AAI(R) mode for one atrial cycle to check/test for intact AV conduction. If intact AV conduction is not found (i.e., if the test for intact AV conduction fails, and thus it is determined that there is AV block), the MVP algorithm reverts to the DDD(R) mode for a further period of time (e.g., two minutes). Then, after the further period of time (e.g., two minutes), the algorithm again switches to the AAI (R) mode for one atrial cycle to again check/test for intact conduction. Each period of time during which DDD(R) pacing is performed can be referred to as the DDD mode pacing interval. The algorithm doubles the DDD mode pacing interval after each failed test (e.g., from 1 minute, to 2 minutes, to 4 minutes, to 8 minutes, etc.), up to a maximum of 16 hours, then tests every 16 hours thereafter.

When using the MVP algorithm, patients could become symptomatic because of frequent dropped beats caused when retesting for intact AV conduction. Further, at least some patients with an implanted cardiac device using the MVP algorithm have experienced other symptoms relating to the MVP algorithm. One such problem occurs when premature ventricular contractions (PVCs) cause retrograde conductions. More specifically, the MVP algorithm, when operating in the AAI(R) mode, may detect the retrograde events as P-waves. Then, since there is no R-wave afterwards (i.e., following retrograde P-waves) to detect, the device interprets this as skipped beats, and the device may mode switch to the DDD(R) mode. This has resulted in repeated mode switching between the AAI(R) and DDD(R) modes, which has caused patients to become symptomatic. Additionally, the retrograde P waves have caused the AEI interval to be reset, which causes long pauses in the ventricular rhythm (i.e., long pauses between consecutive R-waves), which may also play a role in the patients becoming symptomatic. It would be beneficial if such deficiencies of the MVP algorithm can be overcome.

SUMMARY

Embodiments of the present invention are for use with implantable cardiac devices capable of pacing in AAI(R)

mode and DDD(R) mode. Examples of such devices include those devices that use what is known as the MVP algorithm.

In accordance with an embodiment of the present invention, while an implantable cardiac device is in AAI(R) mode, a ventricular channel is monitored for a premature ventricular contraction (PVC). A PVC can be detected, e.g., if two consecutive ventricular events are detected in the ventricular channel without an intervening atrial event being detected in the atrial channel. Here, the second of the two consecutive ventricular events detected without an intervening atrial event is the PVC. A PVC may also be detected, e.g., if a ventricular event is detected in the ventricular channel, but an atrial event is not detected in the atrial channel within a specified time period preceding the ventricular event. Other techniques for detection of a PVC are also possible.

In response to detecting a PVC while the device is in AAI(R) mode, a refractory period is triggered (i.e., started) in the atrial channel to prevent a retrograde atrial event that may occur due to the PVC from resetting an atrial escape interval (AEI). This reduces long pauses in the ventricular rhythm that may occur due to inappropriate resetting of the AEI, during the AAI(R) mode.

In accordance with an embodiment, during such an aforementioned relative refractory period in the atrial channel (that is triggered in response to detecting a PVC), the atrial channel is monitored for a retrograde atrial event that may occur due to the PVC. If a retrograde atrial event is detected, then the refractory period in the atrial channel is terminated, and an antegrade conduction restoration interval (ACRI) is started. The ACRI is a programmed period that specifies how long to wait after a retrograde atrial event is detected before pacing the atrium. Additionally, if a retrograde atrial event is detected during the refractory period, the AEI can also be terminated. Thereafter, the atrium is paced if the ACRI expires before an atrial event is sensed in the atrial channel.

In accordance with an embodiment, when detecting the absence of AV conduction (e.g., by determining if two consecutive atrial events are detected in the atrial channel without an intervening ventricular event being detected in the ventricular channel), a retrograde atrial event is not recognized as an atrial event, to thereby reduce and preferably minimize unnecessary mode switching from AAI mode to DDD mode.

This description is not intended to be a complete description of, or limit the scope of, the invention. Other features, aspects, and objects of the invention can be obtained from a review of the specification, the figures, and the claims.

DETAILED DESCRIPTION

Figure 1:
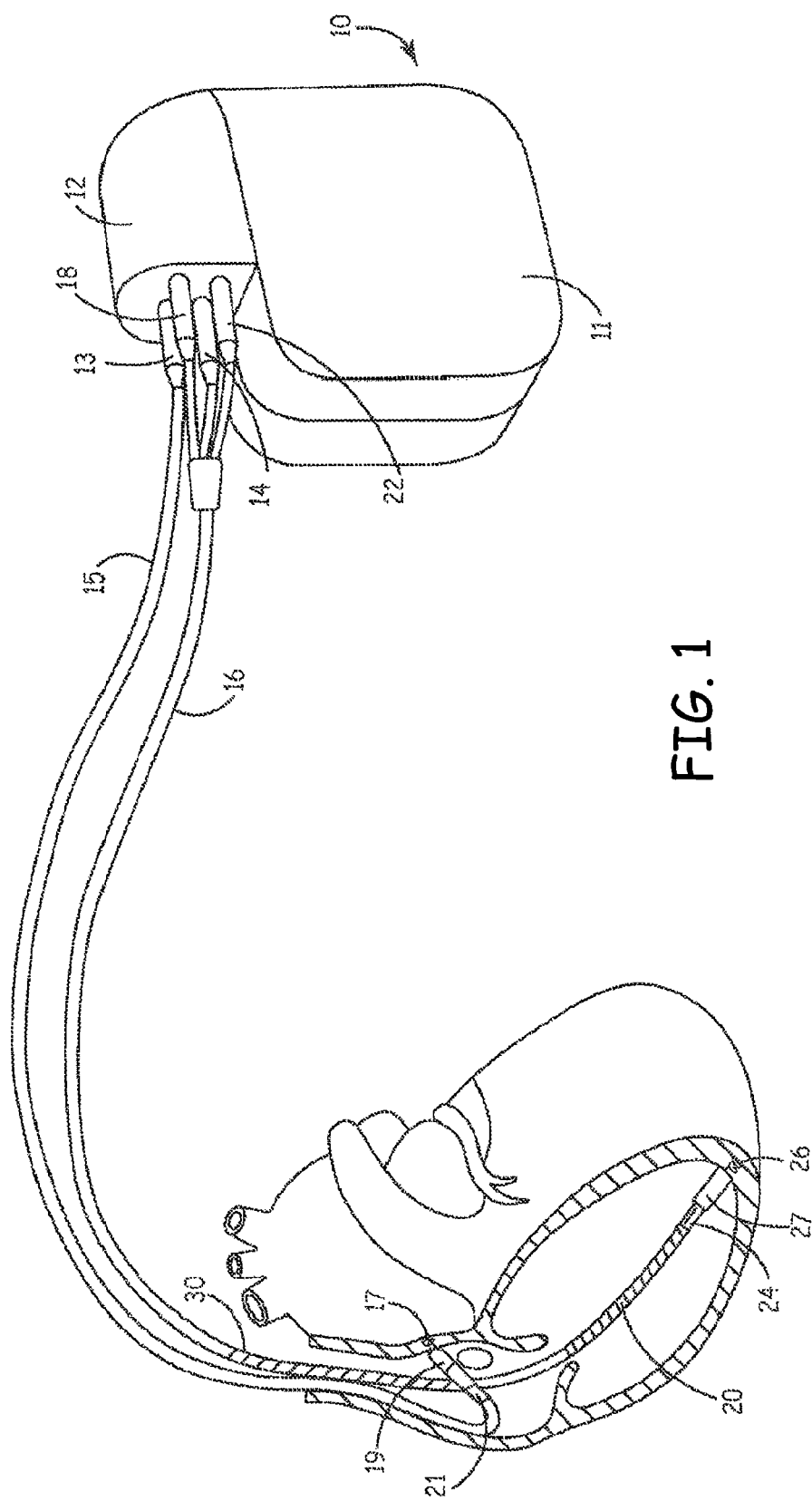
FIG. 1 is an illustration of an exemplary implantable cardiac device in which embodiments of the present invention can be implemented.

Referring now to FIG. 1, there are illustrated an implantable cardiac device 10 and leads 15 and 16, making up the system. The implantable cardiac device 10 can be an implantable cardioverter defibrillator with pacemaker capabilities, or the device 10 can primarily be a pacemaker. It should be appreciated that such a device may include pacing, defibrillation, cardioversion, and/or other therapies alone or in any combination. The leads shown are illustrative, it being noted that other specific forms of leads can be used. Ventricular lead 16 as illustrated has, located adjacent to the distal end, an extendable helix electrode 26 and a ring electrode 24, the helix electrode being mounted retractably within an insulative head 27. Electrodes 24 and 26 are used for bipolar ventricular pacing and for bipolar sensing of ventricular depolarizations. While electrodes 24 and 26 may be used for bipolar pacing and sensing, electrode 26 may be used in conjunction with the surface of device casing 11, which surface acts as a common or indifferent electrode in what is termed unipolar operation. Ventricular lead 16 also carries a coil electrode 20, sometimes referred to as the RV (right ventricular) coil, for delivering defibrillation and/or cardioversion pulses. Coil electrode 20 is positioned on lead 16 so that when the distal tip is at the apex of the ventricle, coil 20 is positioned in the right ventricle. Lead 16 may also carry, optionally, an SVC coil 30, which can be used for applying cardioversion pulses. Lead 16 carries respective concentric coil conductors (not shown), separated from one another by appropriate means such as tubular insulative sheaths and running the length of the lead for making electrical connection between the implantable cardiac device 10 and respective ones of electrodes 20, 24, 26 and 30.

Atrial lead 15 as illustrated includes an extendable helix electrode 17 and a ring electrode 21, the helix electrode being mounted retractably within an insulative head 19. Electrodes 17 and 21 are used for bipolar atrial pacing and for sensing atrial depolarizations. While electrodes 17 and 21 may be used for bipolar pacing and sensing, electrode 17 may be used in conjunction with the surface of device casing 11, which surface acts as a common or indifferent electrode in what is termed unipolar operation. Note that, in this example, atrial lead 15 is not equipped with coils for use in the sensing and delivery of cardioversion of defibrillation pulses. This is not meant to preclude the inclusion of such applications that may be used advantageously with embodiments of the present inventions.

The implantable cardiac device 10, is shown in combination with atrial and ventricular leads, with the lead connector assembly 13, 14, 18, and 22 being inserted into the connector block 12 of the device 10. A specific example of a defibrillation pulse generator that may be used in conjunction with the present ventricular lead is disclosed in U.S. Pat. No. 4,953, 551. Other implantable cardiac device type units can be used; reference is made to U.S. Pat. Nos. 5,163,427 and 5,188,105 as disclosing illustrative forms of apparatus for delivering cardioversion and defibrillation pulses.

Figure 2:
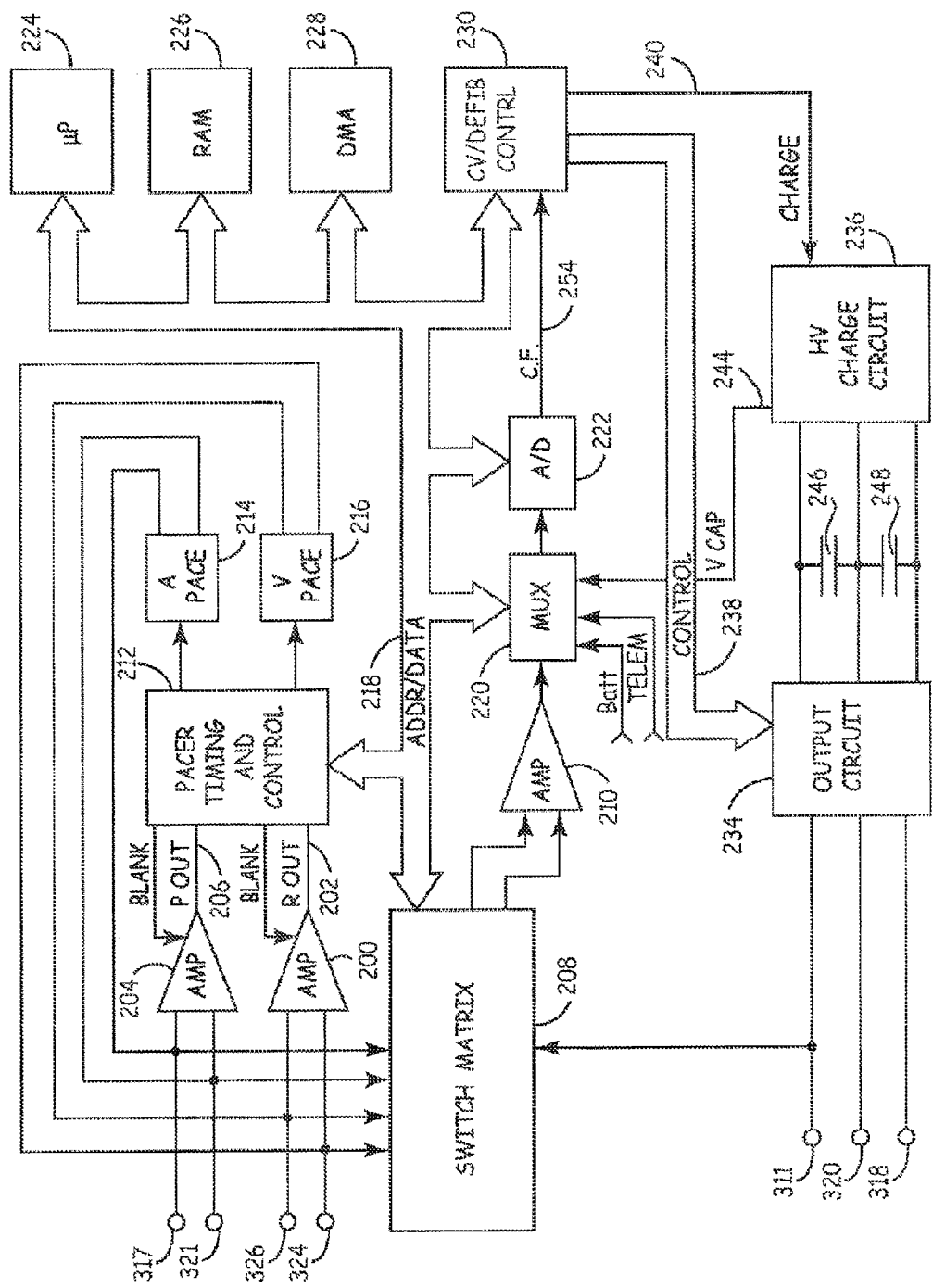
FIG. 2 is a block, functional diagram of an implantable cardiac device that can be used to carry out the features of the present invention.

FIG. 2 is a functional schematic diagram of an implantable pacemaker/cardioverter/defibrillator in which embodiments of the present invention may usefully be practiced. This diagram should be taken as exemplary of the type of device in which the embodiments of the present invention may be embodied, and not as limiting, as it is believed that the embodiments of the present invention may usefully be practiced in a wide variety of device implementations, including devices providing therapies for treating atrial arrhythmias instead of or in addition to ventricular arrhythmias, cardioverters and defibrillators which do not provide anti-tachycardia pacing therapies, anti-tachycardia pacers which do not provide cardioversion or defibrillation, and devices which deliver different forms of anti-arrhythmia therapies such as nerve stimulation or drug administration.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to electrode 16, and is the uninsulated portion of the housing of the implantable pacemaker/cardioverter/defibrillator. Electrode 320 corresponds to electrode 20 and is a defibrillation electrode located in the right ventricle. Electrode 318 corresponds to electrode 30 and is a defibrillation electrode located in the superior vena cava. Electrodes 324 and 326 correspond to electrodes 24 and 26, and are used for sensing and pacing in the ventricle. Electrodes 317 and 321 correspond to electrodes 17 and 21 and are used for pacing and sensing in the atrium.

Electrodes 311, 318 and 320 are coupled to high voltage output circuit 234. Electrodes 324 and 326 are located on or in the ventricle and are coupled to the R-wave amplifier 200, which can take the form of an automatic gain controlled amplifier providing an adjustable sensing threshold as a function of the measured R-wave amplitude. A signal is generated on R-out line 202 whenever the signal sensed between electrodes 324 and 326 exceeds the present sensing threshold. The amplifier 200 and the ventricular pacing circuitry 216, discussed below, can be parts of the ventricular channel More generally, that ventricular channel includes circuitry for generating pacing pulses that are delivered to the ventricles, and sensing circuitry for sensing cardiac signals in the ventricles.

Electrodes 317 and 321 are located on or in the atrium and are coupled to the P-wave amplifier 204, which can also take the form of an automatic gain controlled amplifier providing an adjustable sensing threshold as a function of the measured P-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel et al., issued Jun. 2, 1992, for an Apparatus for Monitoring Electrical Physiologic Signals, incorporated herein by reference in its entirety. The amplifier 204 and the atrial pacing circuitry 214, discussed below, can be parts of the atrial channel. More generally, that atrial channel includes circuitry for generating pacing pulses that are delivered to the atrium, and sensing circuitry for sensing cardiac signals in the atrium.

Switch matrix 208 is used to select which of the available electrodes are coupled to wide band (0.5-200 Hz) amplifier 210 for use in signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal-processing methodologies known to the art.

The remainder of the circuitry is dedicated to the provision of cardiac pacing, cardioversion and defibrillation therapies, and, for purposes of the embodiments of the present invention may correspond to circuitry known in the prior art. An exemplary apparatus is disclosed of accomplishing pacing, cardioversion and defibrillation functions follows. The pacer timing/control circuitry 212 includes programmable digital counters which control the basic time intervals associated with pacing modes, such as AAI(R) and DDD(R) and other modes of single and dual chamber pacing well known to the art. Circuitry 212 also controls escape intervals associated with anti-tachyarrhythmia pacing in both the atrium and the ventricle, employing any anti-tachyarrhythmia pacing therapies known to the art.

Intervals defined by pacing circuitry 212 include atrial and ventricular pacing escape intervals, the refractory periods during which sensed P-waves and R-waves will not restart the escape pacing interval timing. The durations of these intervals are determined by microprocessor 224, in response to stored data in memory 226 and are communicated to the pacing circuitry 212 via address/data bus 218. Pacer circuitry 212 also determines the amplitudes and pulse widths of the cardiac pacing pulses under control of microprocessor 224.

During pacing, the escape interval timers within pacer timing/control circuitry 212 are reset upon sensing of R-waves and P-waves as indicated by signals on lines 202 and 206, and in accordance with the selected mode of pacing on timeout trigger generation of pacing pulses by pacer output circuitry 214 and 216, which are coupled to electrodes 317, 321, 324 and 326. The escape interval timers are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval timers when reset by sensed R-waves and/or P-waves may be used to measure the durations of R-R intervals, P-P intervals, P-R intervals, and R-P intervals, which measurements are stored in memory 226 and used in conjunction with embodiments of the present invention to diagnose the occurrence of a variety of tachyarrhythmias, as discussed in more detail below.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. A portion of the memory 226 may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

The arrhythmia detection method of the implantable cardiac device may include prior art tachyarrhythmia detection algorithms. As described below, the entire ventricular arrhythmia detection methodology of presently available Medtronic pacemaker/cardioverter/defibrillators can be employed as part of the arrhythmia detection and classification method. However, any of the various arrhythmia detection methodologies known to the art, might also be usefully employed in alternative embodiments of the implantable cardiac device.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval timers therein and to define refractory periods during which detection of R-waves and P-waves is ineffective to restart the escape interval timers. Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 7,726,380, issued to Vollmann et al. on Feb. 23, 1988 and U.S. Pat. No. 4,587,970, issued to Holley et al. on May 13, 1986, all of which are incorporated herein by reference in their entireties may also be used.

In the event that generation of a cardioversion or defibrillation pulse is required, microprocessor 224 employs the escape interval timer to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240 2/12. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105 by Keimel, issued Feb. 23, 1993, and incorporated by reference in its entirety. If atrial defibrillation capabilities are included in the device, appropriate systems for delivery and synchronization of atrial cardioversion and defibrillation pulses and for controlling the timing functions related to them may be found in PCT Pat. Application No. WO92/18198 by Adams et al., published Oct. 29, 1992, and in U.S. Pat. No. 4,316,472 by Mirowski et al., issued Feb. 23, 1982, both incorporated herein by reference in their entireties.

However, any known cardioversion or defibrillation pulse control circuitry is believed usable in conjunction with embodiments of the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al, cited above, and in U.S. Pat. No. 4,375,817, issued to Engle et al, all incorporated herein by reference in their entireties may also be employed.

In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse. An example of output circuitry for delivery of biphasic pulse regimens may be found in the above cited patent issued to Mehra and in U.S. Pat. No. 4,727,877, incorporated by reference in its entirety.

An example of circuitry which may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al. on Sep. 4, 1990 or U.S. Pat. No. 4,800,883, issued to Winstrom on Jan. 31, 1989 both incorporated herein by reference in their entireties, may also be used in conjunction with a device embodying embodiments of the present invention for delivery of biphasic pulses.

In modern implantable cardioverter/defibrillators, the physician, from a menu of therapies that are typically provided, programs the specific therapies into the device. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher energy cardioversion pulse may be selected for subsequent delivery. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is below a preset threshold. The references cited above in conjunction with descriptions of prior art tachycardia detection and treatment therapies are applicable here as well.

In the event that fibrillation is identified, the typical therapy will be the delivery of a high amplitude defibrillation pulse, typically in excess of 5 joules. Lower energy levels may be employed for cardioversion. As in the case of currently available implantable cardiac device's, and as discussed in the above-cited references, it is envisioned that the amplitude of the defibrillation pulse may be incremented in response to failure of an initial pulse or pulses to terminate fibrillation. Prior art patents illustrating such pre-set therapy menus of anti-tachyarrhythmia therapies include the above-cited U.S. Pat. No. 4,830,006, issued to Haluska et al., U.S. Pat. No. 4,727,380, issued to Vollmann et al. and U.S. Pat. No. 4,587,970, issued to Holley et al.

Figure 3:
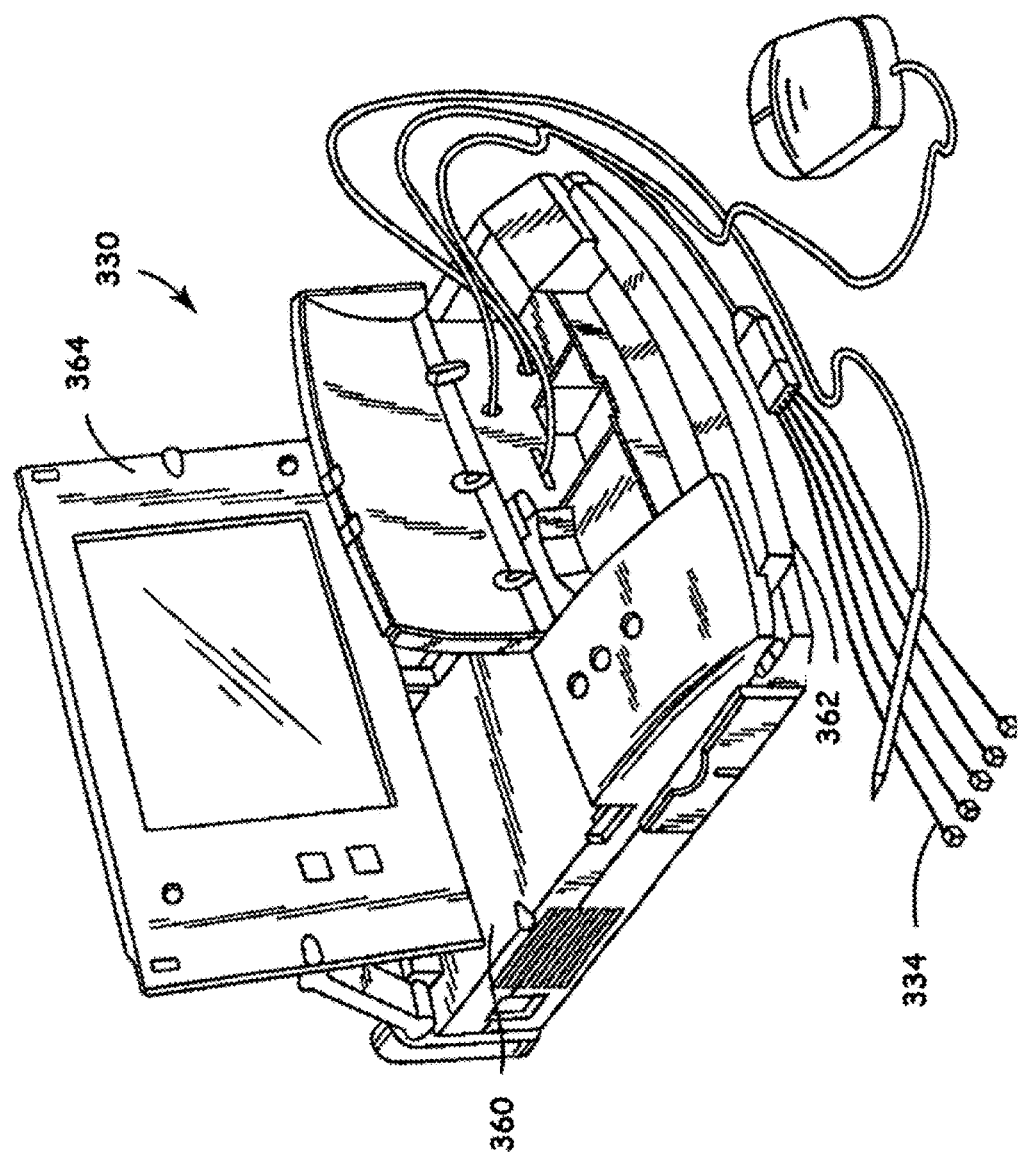
FIG. 3 is a perspective view of the exemplary external programming unit of FIG. 1.

FIG. 3 is a perspective view of an exemplary programming unit 330, which is also known as a programmer. Internally, programmer 330 includes a processing unit (not shown in the Figure) that can be personal computer type motherboard, e.g., a computer motherboard including an Intel Pentium 3 microprocessor and related circuitry such as digital memory. The details of design and operation of the programmer's computer system will not be set forth in detail in the present disclosure, as it is believed that such details are well-known to those of ordinary skill in the art.

Referring to FIG. 3, programmer 330 comprises an outer housing 360, which is preferably made of thermal plastic or another suitably rugged yet relatively lightweight material. A carrying handle, designated generally as 362 in FIG. 2, is integrally formed into the front of housing 360. With handle 362, programmer 330 can be carried like a briefcase.

An articulating display screen 364 is disposed on the upper surface of housing 360. Display screen 364 folds down into a closed position (not shown) when programmer 330 is not in use, thereby reducing the size of programmer 330 and protecting the display surface of display 364 during transportation and storage thereof.

A floppy disk drive is disposed within housing 360 and is accessible via a disk insertion slot (not shown). A hard disk drive is also disposed within housing 360, and it is contemplated that a hard disk drive activity indicator, (e.g., an LED, not shown) could be provided to give a visible indication of hard disk activation.

As would be appreciated by those of ordinary skill in the art, it is often desirable to provide a means for determining the status of the patient's conduction system, heart rhythm, electrical activation and a number of other parameters. Normally, programmer 330 is equipped with external ECG leads 334.

The programmer 330 can be equipped with an internal printer (not shown) so that a hard copy of a patient's ECG or of graphics displayed on the programmer's display screen 364 can be generated. Several types of printers, such as the AR-100 printer available from General Scanning Co., are known and commercially available.

In the perspective view of FIG. 3, programmer 330 is shown with articulating display screen 364 having been lifted up into one of a plurality of possible open positions such that the display area thereof is visible to a user situated in front of programmer 330. Articulating display screen is preferably of the LCD or electro-luminescent type, characterized by being relatively thin as compared, for example, a cathode ray tube (CRT) or the like.

As would be appreciated by those of ordinary skill in the art, display screen 64 is operatively coupled to the computer circuitry disposed within housing 360 and is adapted to provide a visual display of graphics and/or data under control of the internal computer.

Programmer 330 described herein with reference to FIG. 2 is described in more detail in U.S. Pat. No. 5,345,362 issued to Thomas J. Winkler, entitled Portable Computer Apparatus With Articulating Display Panel, which patent is hereby incorporated herein by reference in its entirety. The Medtronic Model 9790 programmer is the implantable device-programming that can be used to program an implantable cardiac device to perform embodiments of the present invention.

As mentioned, the implantable cardiac device 10 may include various cardiac rhythm management capabilities such as sensing and pacing. As such, the implantable cardiac device 10 operates under a given set of rules defined by the mode that the implantable cardiac device 10 is in at a given time. The mode selected will depend upon the physiologic needs of the patient, which could vary over time. Thus, the implantable cardiac device 10 may selectively switch between modes to best address such conditions.

Those of ordinary skill in the art will appreciate that implantable cardiac device 10 may include numerous other components and subsystems.

SPECIFIC EMBODIMENTS OF THE PRESENT INVENTION

The above described device 10 is an example of an implantable device that can pace a patient in accordance with the MVP algorithm described in the above Background section. As described above, when implementing the MVP algorithm, AAI(R) mode is the primary mode of pacing. In the AAI(R) mode, sensing occurs in the atrium, pacing occurs in the atrium, and atrial pacing is inhibited if an intrinsic atrial event (i.e., a P wave) is detected within a programmed atrial escape interval (AEI). However, unlike the typical AAI(R) mode of operation, in the MVP algorithm ventricular events are also sensed to provide for ventricular backup. So long as a ventricular event is sensed anywhere within a given A-A interval, the pacing mode remains as the AAI(R) mode. However, ventricular backup pacing occurs as needed, in the presence of a transient loss of AV conduction. More specifically, when a P wave is blocked (i.e., not conducted through the AV node), resulting in an atrial event not being sensed within the A-A interval, a single ventricular pace is provided, which can be synchronized on the next P wave.

When there is persistent loss of AV conduction, the pacing mode is switched to the DDD(R) mode. For example, if there is loss of AV conduction for 2 out of 4 pacing cycles (e.g., 2 out of 4 A-A intervals), the algorithm performs a mode-switch to the DDD(R) mode. Pacing occurs in the DDD(R) mode for a period of time (e.g., 1 minute), after which the algorithm checks for the resumption of intact conduction, e.g., by switching to the AAI(R) mode for one atrial cycle to check/test for intact AV conduction. If intact AV conduction is not found (i.e., if the test for intact AV conduction fails, and thus it is determined that there is AV block), the MVP algorithm reverts to the DDD(R) mode for a further period of time (e.g., two minutes). Then, after the further period of time (e.g., two minutes), the algorithm again switches to the AAI (R) mode for one atrial cycle to again check/test for intact conduction. The algorithm doubles the DDD mode pacing interval after each failed test (e.g., from 1 minute, to 2 minutes, to 4 minutes, to 8 minutes, etc.), up to a maximum of 16 hours, then tests every 16 hours thereafter.

As explained above, when using the MVP algorithm, patients could become symptomatic because of frequent dropped beats caused when retesting for intact AV conduction. Further, at least some patients with an implanted cardiac device using the MVP algorithm have experienced other symptoms relating to the MVP algorithm. One such problem occurs when premature ventricular contractions (PVCs) cause retrograde conductions. More specifically, the MVP algorithm, when operating in the AAI(R) mode, may detect the retrograde events as P-waves. Then, since there is no R-wave afterwards (i.e., following retrograde P-waves) to detect, the device interprets this as a skipped beats, and the device may mode switch to the DDD(R) mode. This is described with reference to the timing diagram of FIG. 4. This has resulted in repeated mode switching between the AAI(R) and DDD(R) modes, which has caused patients to become symptomatic. Specific embodiments of the present invention overcome this deficiency of the MVP algorithm, as described with reference to the timing diagrams of FIGS. 5 and 6.

Additionally, when using the MVP algorithm, retrograde P waves have caused the AEI interval to be reset, which causes long pauses in the ventricular rhythm (i.e., long pauses between consecutive R-waves), which may also play a role in the patients becoming symptomatic. This is also described below with reference to the timing diagram of FIG. 4. Embodiments of the present invention can be used to overcome these further deficiencies of the MVP algorithm, as also described below with reference to the timing diagrams of FIGS. 5 and 6.

In AAI(R) mode, a pacemaker (or other implantable device) will pace the atrium in the absence of an atrial sensed event, as indicated by the first letter A. Additionally, the pacemaker will sense in the atrium, as indicated by the second letter A. Further, as indicated by the third letter 1, the pacemaker will inhibit pacing in the chamber that is paced, the atrium in this instance. The final letter in parenthesis, R, implies that the device may be rate responsive, that is, altering the atrial rate in response to an artificial sensor, such as a Piezo-electrical crystal, accelerometer, minute ventilation, etc.

As mentioned in the Background section, when using the MVP algorithm ventricular events are also sensed during the so called AAI(R) mode, and thus this mode may alternatively be referred to as an ADI(R) mode, or AAI(R)+mode, because there is ventricular backup. Going forward, the term AAI(R) mode is used to describe the primary atrial pacing mode of the MVP algorithm, which as described above, can include monitoring of the ventricular channel and backup pacing in the ventricles in response to transient losses of AV conduction.

In DDD(R) mode, a pacemaker (or other implantable device), will pace the atrium and ventricles, as indicated by the first letter D. Additionally, the pacemaker will sense in the atrium and the ventricles, as indicated by the second letter D. Further, as indicated by the third letter D, the response in the atrium and ventricles can be inhibition or triggering (i.e., the third D stands for dual response). The DDD(R) mode is very useful when a persistent loss of AV conduction actually occurs. However, as can be appreciated from the description in the above Background section, it is desirable to use the AAI(R) mode instead of the DDD(R) mode when there has not been an actual loss of AV conduction, to allow for normal ventricular activation.

Figure 4:
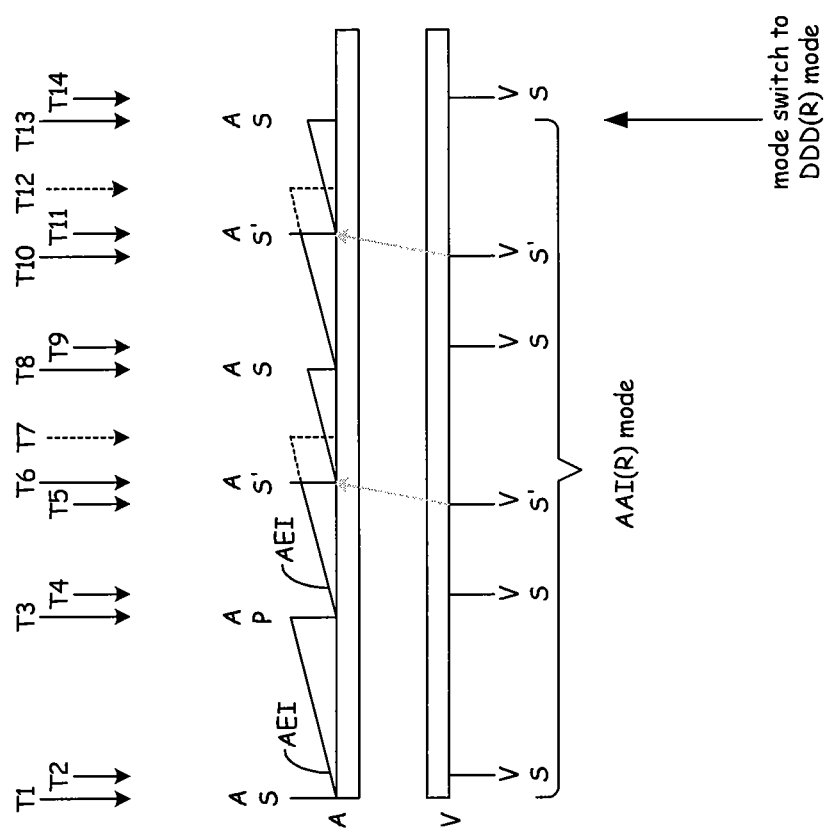
FIG. 4 is a timing diagram of AAI(R) operation which results in an unnecessary mode switch to DDD(R) mode.

FIG. 4 will now be used to describe how the MVP algorithm, when operating in the AAI(R) mode, may mistakenly detect the retrograde atrial events as normal P-waves, which has resulted in repeated mode switching between the AAI(R) and DDD(R) modes, causing some patients to become symptomatic. Referring to FIG. 4, the upper plot labeled A is used to represent atrial activity in the atrial channel, and the lower plot labeled B is used to represent ventricular activity in the ventricular channel. Note that conventional blanking and refractory periods that are used during AAI(R) mode, which are not directly related to embodiments of the present invention, are not shown in FIGS. 4-6, so as to not clutter up the figures. Such conventional blanking and refractory periods that are used during AAI(R) mode include, but are not limited to, the atrial blanking period (ABP) and the atrial refractory period (ARP) that are both triggered in the atrial channel when an atrial pace (AP) is delivered.

Referring to FIG. 4, at time T1, an intrinsic atrial event (AS) is sensed in the atrial channel, and an atrial escape interval (AEI) is started. When in AAI(R) mode, the AEI is a programmed time period that specifies how long to wait after an atrial sensed or paced event before pacing the atrium. In contrast, the AEI during DDD(R) mode is a programmed time period that specifies how long to wait after a ventricular sensed or paced event before pacing the atrium. When in AAI(R) mode, the AEI is reset when an atrial event is sensed in the atrial channel, or when the atrium is paced. In other words, an atrial pace (AP) is delivered at the end of the AEI, unless inhibited due in intrinsic atrial event AS occurring during the AEI.

At time T2 an intrinsic ventricular event (VS) is sensed in the ventricular channel. At time T3, when the AEI expires, an atrial pace AP is delivered. At time T4, an intrinsic ventricular event VS is sensed in the ventricular channel.

At time T5, a ventricular event VS', which is a premature ventricular contraction (PVC), is sensed in the ventricular channel. The PVC causes a retrograde atrial event AS' to be sensed in the atrial channel at time T6. The retrograde atrial event AS' resets the AEI, so that an atrial pace AP is not delivered at time T7 (i.e., when the AEI would have expired were it not reset). Thereafter, at time T8 an atrial event AS is sensed in the atrial channel, and a ventricular event VS is sensed in the ventricular channel at time T9.

Note that the device interprets, as a loss of AV conduction, the failure to sense a ventricular event in the ventricular channel between the atrial event AS' sensed at time T6 and the atrial event AS sensed at time T8. Also, by not pacing the atrium at time T7 (because the AEI was reset by the sensed retrograde atrial event), the following intrinsic ventricular event is delayed, which causes a long pause in the ventricular rhythm (i.e., a long pause between consecutive R-waves).

At time T10, a ventricular event VS', which is another PVC, is sensed in the ventricular channel. Again, the PVC causes a retrograde atrial event AS' to be sensed in the atrial channel, as shown at time T11. The retrograde atrial event AS' resets the AEI, so that an atrial pace AP is not delivered at time T12 (i.e., when the AEI would have expired were it not reset). Thereafter, at time T13 an atrial event AS is sensed in the atrial channel, and a ventricular event VS is sensed in the ventricular channel at time T14.

Here the device interprets, as a second loss of AV conduction within the past four cardiac cycles, the failure to sense a ventricular event in the ventricular channel between the atrial event AS' sensed at time T11 and the atrial event AS sensed at time T13, which will cause the device to switch to DDD(R) mode. This is undesirable, since an intrinsic ventricular even had actually followed every paced or sensed atrial event that was not a retrograde atrial event, meaning that AV conduction was never actually lost. Also, by not pacing the atrium at time T13, another long pause occurs in the ventricular rhythm.

After the mode switch, pacing occurs in the DDD(R) mode for a period of time (e.g., 1 minute), after which the algorithm checks for the resumption of intact conduction, e.g., by switching to the AAI(R) mode for one atrial cycle to check/test for intact AV conduction. If intact AV conduction is not found (i.e., if the test for intact AV conduction fails, and thus it is determined that there is AV block), the MVP algorithm reverts to the DDD(R) mode for a further period of time (e.g., two minutes), and thereafter periodically switches to AAI(R) mode until intact AV conduction is detected, as was described in more detail above in the Background section. This has resulted in repeated mode switching between the AAI(R) and DDD(R) modes, as wells as long pauses in the ventricular rhythm (as just explained with reference to FIG. 4), both of which may play a role in the patients becoming symptomatic.

Figure 5:
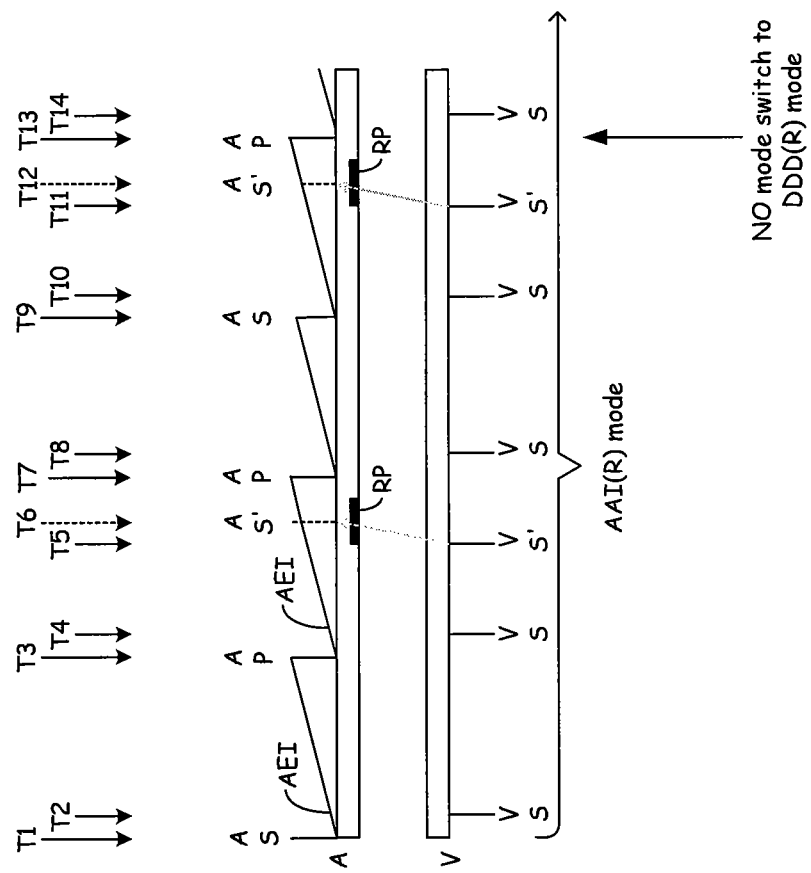
FIG. 5 is a timing diagram that is shows how embodiments of the present invention can be used to improve upon the AAI(R) operation described with reference to FIG. 4.

FIG. 5 will now be used to explain how an embodiment of the present invention can be used to reduce (and hopefully prevent) unnecessary mode switching that occurs due to retrograde atrial events that result from PVCs. This embodiment will also have the effect of reducing (and hopefully preventing) the long pauses in the ventricular rhythm that result from the AEI being reset when a retrograde atrial event is sensed. Further, this embodiment should also have the effect of reducing unnecessary ventricular pacing that may occur due to unnecessary mode switching from AAI(R) mode to DDD(R) mode that occurs due to retrograde atrial events that result from PVCs.

Referring to FIG. 5, at time T1 an intrinsic atrial event (AS) is sensed in the atrial channel, and an AEI is started. At time T2 an intrinsic ventricular event (VS) is sensed in the ventricular channel. At time T3, when the AEI expires, an atrial pace AP is delivered. At time T4 an intrinsic ventricular event VS is sensed in the ventricular channel.

At time T5 a ventricular event VS', which is a PVC, is sensed in the ventricular channel. Additionally, at time T5, in response to detecting the PVC while the device is in AAI mode, a refractory period (RP) is triggered (i.e., started) in the atrial channel to prevent a retrograde P-wave that may occur due to the PVC from resetting the AEI. Accordingly, when the PVC causes a retrograde atrial event AS' to show up the atrial channel at time T6, the retrograde atrial event AS' will not reset the AEI since the retrograde atrial event AS' occurs during the RP that was triggered in accordance with an embodiment of the present invention. Since the AEI was not reset, an atrial pace AP is delivered at time T7 when the AEI expires. Thereafter, at time T8 an intrinsic ventricular event VS is sensed in the ventricular channel.

Note that the due to the RP in the atrial channel (that was triggered in response to the PVC being detected in the ventricular channel at time T5), the retrograde atrial event that occurred at time T6 does not result in device thinking that it detected a loss of AV conduction. This is described in some more detail below. Also, because the atrium was paced at time T7 (because the AEI was not reset by the retrograde atrial event), the following intrinsic ventricular event is not delayed, thereby avoiding the long pause in the ventricular rhythm that was described above with reference to FIG. 4.

Still referring to FIG. 5, at time T9 an intrinsic atrial event AS is sensed in the atrial channel, and at time T10 an intrinsic ventricular event VS is sensed in the ventricular channel.

Thereafter, at time T11 a ventricular event VS', which is another PVC, is sensed in the ventricular channel. Again, in response to detecting the PVC while the device is in AAI mode, an RP is started in the atrial channel. Accordingly, when the PVC causes a retrograde atrial event AS' to show up the atrial channel at time T12, the retrograde atrial event AS' will not reset the AEI since the retrograde atrial event AS' occurs during the RP. Since the AEI is not reset, an atrial pace AP is delivered at time T13 when the AEI expires (or earlier, if an intrinsic atrial event occurs after the RP expires, but before the AEI expires). Thereafter, at time T14 an intrinsic ventricular event VS is sensed in the ventricular channel.

Again, due to the RP in the atrial channel (that was triggered in response to the PVC being detected in the ventricular channel at time T11), the retrograde atrial event that occurred at time T12 does not result in device thinking that it detected a loss of AV conduction. Also, because the atrium was paced at time T13 (because the AEI was not reset by the retrograde atrial event), a long pause in the ventricular rhythm is again avoided.

Here since neither PVC resulted in the device thinking that it had lost AV conduction, there is no inappropriate switch to DDD(R) mode following the two PVCs that resulted in retrograde atrial events. Indeed, an intrinsic ventricular event followed every paced or sensed atrial event that was not a retrograde atrial event, and thus there was no need to switch to DDD(R) mode. Also, explained above, the retrograde atrial events did not delay pacing in the atrium, and thus did not result in long pauses in the ventricular rhythm.

The RP triggered in the atrial channel, in response to a PVC being detected in the ventricular channel while the device is in AAI(R) mode, should be long enough to prevent retrograde atrial events that may show up in the atrial channel from causing the AEI from being reset. However, the RP should be short enough to prevent normal atrial events from being interpreted as retrograde atrial events. In accordance with an embodiment, the length of the RP is programmable within the range normally associated with PVARP (post ventricular atrial refractory period), which is between approximately 200 and 500 msec, with a preferred length of about 300 msec.

The RP triggered in the atrial channel (in response to a PVC being detected in the ventricular channel while the device is in AAI(R) mode) is similar to a post-ventricular atrial refractory period (PVARP) in that the both types of refractory periods are triggered by a ventricular event detected in the ventricular channel. However, the typical PVARP is only triggered while the device is in DDD(R) or DDI(R) modes, i.e., a dual chamber pacing mode. In other words, the PVARP has not conventionally been used during AAI(R) mode.

As mentioned above, when using the MVP algorithm, mode switching from AAI(R) mode to DDD(R) mode occurs if AV conduction is absent in N out of the last M pacing cycles, where N and M are integers and N<M. Typically, N=2 and M=4. The absence of AV conduction can be detected if two consecutive atrial events are detected in the atrial channel without an intervening ventricular event being detected in the ventricular channel. In accordance with specific embodiments of the present invention, in order to avoid unnecessary mode switching from MI(R) mode to DDD(R) mode, when determining whether two consecutive atrial events are detected in the atrial channel without an intervening ventricular event being detected in the ventricular channel (for the purpose of detecting whether there is an absence of AV conduction), a retrograde atrial event is not recognized as (i.e., not treated or interpreted as) an atrial event. In accordance with an embodiment, any atrial event exceeding a detection threshold that is sensed during the RP (that is triggered in response to detecting a PVC in the ventricular channel) is assumed to be a retrograde atrial event AS'.

A PVC is ventricular contraction not initiated by the atrium, i.e., not resulting from normal propagation of an action potential that propagates from the atrium through the atrioventricular node (AV node) and the atrioventricular bundle (AV bundle or His bundle) to the ventricles. There are various ways that a PVC can be detected during the AAI(R) mode that includes monitoring of the ventricular channel. In accordance with one embodiment, a PVC is detected if two consecutive ventricular events are detected in the ventricular channel without an intervening atrial event being detected in the atrial channel. Here, the second of the two consecutive ventricular events detected without an intervening atrial event is the PVC. Additionally, or alternatively, a PVC can be detected if a ventricular event is detected in the ventricular channel, but an atrial event is not detected in the atrial channel within a specified time period preceding (e.g., between about 400 and 600 msec) the ventricular event. For another example, since the morphology of a PVC is different than the morphology of a ventricular contraction initiated by the atrium, a morphology analysis can be performed to detected a PVC. Alternative techniques for detected a PVC are also possible, and can be used with embodiments of the present invention.

Referring back to FIG. 5, if a retrograde atrial event AS' occurs prior to the expiration of AEI, but very close in time to the expiration of the AEI, the retrograde atrial event AS' may prevent the atrial pace AP (that is provided at the expiration of the AEI) from capturing the atrium. Specific embodiments of the present invention, described below with reference to the timing diagram of FIG. 6, provide a way to avoid this from happening.

Figure 6:
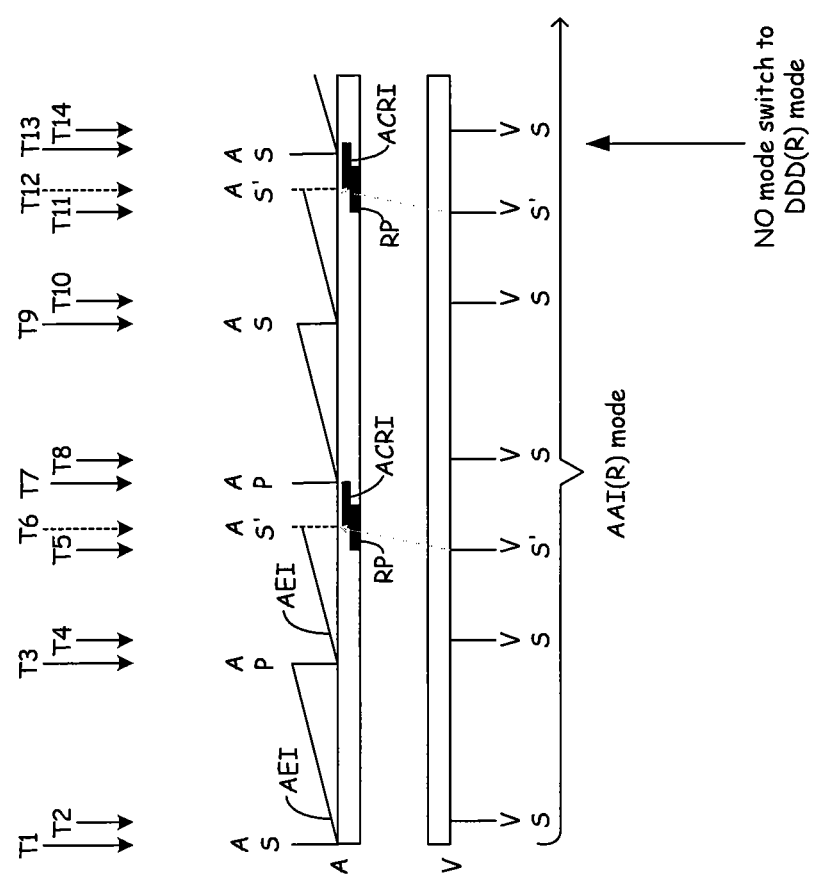
FIG. 6 is a timing diagram that is shows how further embodiments of the present invention can be used to further improve upon the AAI(R) operation described with reference to FIG. 4.

Referring to FIG. 6, in accordance with specific embodiments, during the RP in the atrial channel (that is triggered at time T5 in response to detecting a PVC in the ventricular channel during AAI(R) mode), the atrial channel is monitored for a retrograde atrial event that may occur due to the PVC. If a retrograde atrial event is detected during the RP (as occurs at time T6 in FIG. 6), the RP and the AEI in the atrial channel are terminated and an antegrade conduction restoration interval (ACRI) is triggered (i.e., started). The ACRI is a programmed period that specifies how long the device waits after a retrograde atrial event is detected before pacing the atrium.

If an intrinsic atrial event occurs during the ACRI, as occurs for example at time T13 in FIG. 6, then the ACRI is terminated, and the AEI is started.

The ACRI is preferably long enough to allow capture, but short enough to minimize lengthening of the A-A interval. In accordance with specific embodiments, the ACRI is between approximately 200 and 450 msec, and is preferably about 330 msec.

Figure 7:
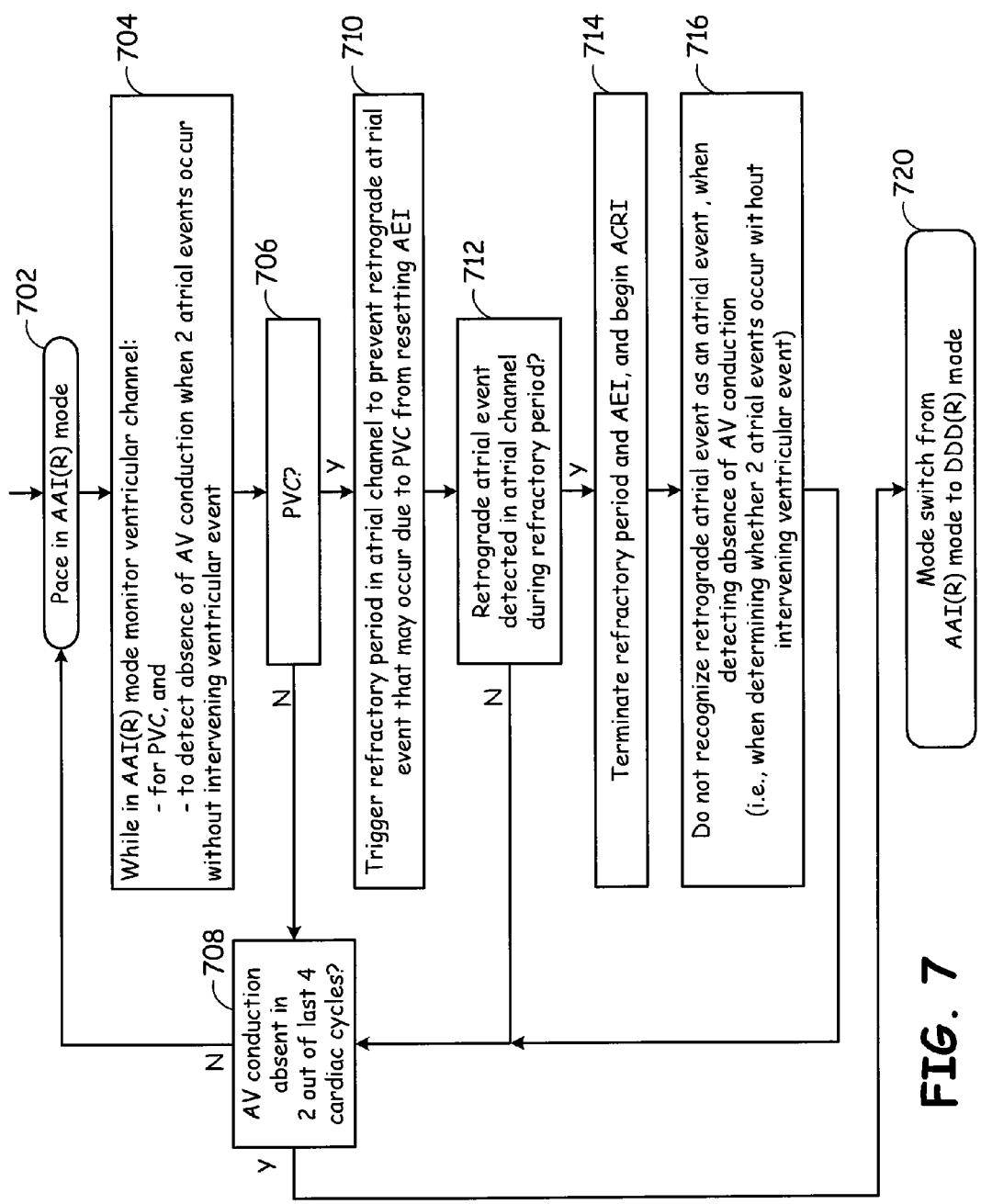
FIG. 7 is a high level flow diagram that is used to summarize various embodiments of the present invention.

Various embodiments of the present invention shall now be summarized with reference to the high level flow diagram of FIG. 7. In the flow diagram of FIG. 7 the various algorithmic steps are summarized in individual "blocks" or "steps". Such blocks describe specific actions or determinations that are made or carried out as the algorithm proceeds. Where a microcontroller (or equivalent) is employed, the flow charts presented herein provide the basis for a "control program" that may be used by such a microcontroller (or equivalent) to effectuate the desired control of an implantable cardiac device. Those skilled in the art may readily write such a control program based on the flow charts and other descriptions presented herein.

As shown at 702, the device is pacing using AAI(R) mode as its primary pacing mode. As indicated at step 704, while in AAI(R) mode, the ventricular channel is monitored for a PVC, as well as to detect the absence of AV conduction when two atrial events are detected in the atrial channel without an intervening ventricular event being detected in the ventricular channel.

At step 706 there is a determination of whether a PVC was detected in the ventricular channel. Some exemplary ways in which to monitor for a PVC were discussed above. If a PVC was not detected, then at step 708 there is a determination of whether AV conduction was absent in 2 out of the last 4 cardiac cycles, or more generally, N out of the last M cardiac cycles. If the answer to step 708 is no, then pacing in AAI(R) mode continues. If the answer to the question of step 708 is yes, then there is a mode switch from AAI(R) mode to DDD (R) mode, as indicated at step 720.

Returning to step 706, if a PVC was detected, then at step 708 a refractory period is triggered in the atrial channel to prevent a retrograde atrial event, that may occur due to the PVC, from resetting the AEI. At step 712, there is a determination of whether a retrograde atrial event is detected in the atrial channel during the refractory period (that was triggered at step 710). Details of how to make this determination were discussed above. If a retrograde atrial event was not detected (i.e., if the answer to the question of step 712 is no), then flow goes to step 708, which was explained above. If a retrograde atrial event was detected (i.e., if the answer to the question of step 712 is yes), then at step 714 the refractory period (that was triggered at step 710) is terminated, the AEI is terminated, and the ACRI is started. As explained above, the ACRI is a programmed period that specifies how long to wait after a retrograde atrial event is detected before pacing the atrium.

As indicated at step 716, when determining whether two atrial events occur without an intervening atrial event, for the purpose of detecting the absence of AV conduction, the detected retrograde atrial event is not recognized as (i.e., not treated or interpreted as) an atrial event for such purpose. This reduces that chance that retrograde atrial events will unnecessarily cause mode switching from AAI(R) mode to DDD (R) mode, as can occur as explained above with reference to FIG. 4.

The modes discussed may be embodied in hardware, firmware, software, code, instructions, or any appropriate format stored in memory or any computer readable medium accessible by the appropriate medical device. The modalities may be incorporated into a device by design or manufacture or may be added to a preexisting device.

Embodiments of the present invention have been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine, separate and/or reorder some of the steps shown in FIG. 7 without substantially changing the overall events and results.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed:

1. A method for use in an implantable cardiac device capable of pacing in AAI(R) mode and DDD(R) mode, the method comprising:
   (a) while the cardiac device is in AAI(R) mode, monitoring a ventricular channel for a premature ventricular contraction (PVC); and
   (b) in response to detecting a PVC while the device is in AAI(R) mode, triggering a refractory period in an atrial channel to prevent a retrograde atrial event, which may occur due to the PVC, from resetting an atrial escape interval (AEI).

2. The method of claim 1, wherein step (a) includes detecting a PVC in response to:
   two consecutive ventricular events being detected in the ventricular channel without an intervening atrial event being detected in the atrial channel, wherein the second of the two consecutive ventricular events detected without an intervening atrial event is the PVC; or
   a ventricular event being detected in the ventricular channel, but an atrial event is not being detected in the atrial channel within a specified time period preceding the ventricular event.

3. The method of claim 1, further comprising:
   (c) detecting the absence of atrioventricular (AV) conduction in response to two consecutive atrial events being detected in the atrial channel without an intervening ventricular event being detected in the ventricular channel, wherein during step (c) a retrograde atrial event is not recognized as an atrial event; and
   (d) mode switching from AAI(R) mode to DDD(R) mode in response to detecting a persistent loss of AV conduction.

4. The method of claim 3, wherein step (d) comprises detecting a persistent loss of AV conduction when AV conduction is absent in N out of the last M pacing cycles, where N and M are integers and N <M.

5. The method of claim 3, wherein step (c) includes identifying an atrial event as a retrograde P-wave when the atrial event is detected during a refractory period in the atrial channel that was triggered in response to detecting a PVC.

6. The method of claim 1, further comprising:
   (c) detecting the absence of atrioventricular (AV) conduction in response to two consecutive atrial events being detected in the atrial channel without an intervening ventricular event being detected in the ventricular channel, wherein during step (c) an atrial event is ignored when the atrial event is detected during a refractory period in the atrial channel that was triggered in response to detecting a PVC; and (d) mode switching from AAI(R) mode to DDD(R) mode in response to a persistent loss of AV conduction being detected.

7. The method of claim 1, further comprising while the cardiac device is in AAI(R) mode, performing ventricular back-up pacing in response to transient losses of atrioventricular (AV) conduction.

8. A method for use in an implantable cardiac device capable of pacing in AAI(R) mode and DDD(R) mode, the method comprising:

(a) while the cardiac device is in AAI(R) mode, monitoring a ventricular channel for a premature ventricular contraction (PVC);

(b) in response to detecting a PVC while the device is in AAI(R) mode, triggering a refractory period in an atrial channel to prevent a retrograde atrial event, which may occur due to the PVC, from resetting an atrial escape interval (AEI);

(c) during a refractory period in the atrial channel that is triggered in response to detecting a PVC, monitoring the atrial channel for a retrograde atrial event that may occur due to the PVC; and (d) in response to detecting a retrograde atrial event during a refractory period in the atrial channel that is triggered in response to detecting a PVC, terminating the refractory period in the atrial channel and beginning an antegrade conduction restoration interval (ACRI), wherein the ACRI is a programmed period that specifies how long to wait after the retrograde atrial event is detected before pacing the atrium.

9. The method of claim 8, wherein step (d) also includes, in response to detecting a retrograde atrial event, terminating the AEI.

10. The method of claim 8, further comprising:
(e) pacing the atrium in response to the ACRI expiring before an atrial event is sensed in the atrial channel.

11. The method of claim 8, wherein the ACRI is between approximately 200 and 450 msec.

12. A method for use in an implantable cardiac device capable of pacing in AAI(R) mode and DDD(R) mode, the method comprising:

(a) pacing in AAI(R) mode by default, but mode switching from AAI(R) mode to DDD(R) mode in response to a persistent loss of atrioventricular (AV) conduction being detected;

(b) while pacing in AAI(R) mode, monitoring a ventricular channel for a premature ventricular contraction (PVC); and (c) in response to a PVC being detected while pacing in AAI(R) mode,
triggering a refractory period in an atrial channel to prevent a retrograde atrial event, which may occur due to the PVC, from resetting an atrial escape interval (AEI), and
monitoring the atrial channel for a retrograde atrial event that may occur due to the PVC; and (d) in response to a retrograde atrial event is being detected in the atrial channel while pacing in AAI(R) mode, terminating the refractory period in the atrial channel and beginning an antegrade conduction restoration interval (ACRI), wherein the ACRI specifies how long to wait after the retrograde atrial event is detected before pacing the atrium.

13. The method of claim 12, further comprising:
(e) pacing the atrium in response to the ACRI expiring before an atrial event is sensed in the atrial channel.

14. The method of claim 12, further comprising:
(e) detecting the absence of AV conduction in response to two consecutive atrial events being detected in the atrial channel without an intervening ventricular event being detected in the ventricular channel, wherein during step (e) a retrograde atrial event is not recognized as an atrial event.

15. The method of claim 12, further comprising:
(e) detecting the absence of AV conduction in response to two consecutive atrial events being detected in the atrial channel without an intervening ventricular event being detected in the ventricular channel, wherein during step (e) an atrial event is ignored when the atrial event is detected during a refractory period in the atrial channel that is triggered in response to detecting a PVC.

16. An implantable cardiac device capable of pacing in AAI(R) mode and DDD(R) mode, comprising:

means for monitoring a ventricular channel for a premature ventricular contraction (PVC), while the cardiac device is in AAI mode; and means for triggering a refractory period in an atrial channel to prevent a retrograde P-wave, which may occur due to the PVC, from resetting an atrial escape interval (AEI), in response to detecting a PVC while the device is in AAI mode.

17. The implantable cardiac device of claim 16, further comprising a means for detecting a PVC in response to:
two consecutive ventricular events being detected in the ventricular channel without an intervening atrial event being detected in the atrial channel, wherein the second of the two consecutive ventricular events detected without an intervening atrial event is the PVC; or
a ventricular event being detected in the ventricular channel, but an atrial event is not being detected in the atrial channel within a specified time period preceding the ventricular event.

18. The method of claim 16, further comprising:
means for performing ventricular back-up pacing in response to transient losses of AV conduction while the cardiac device is in AAI(R) mode.

19. An implantable cardiac device capable of pacing in AAI(R) mode and DDD(R) mode, comprising:
means for monitoring a ventricular channel for a premature ventricular contraction (PVC), while the cardiac device is in AAI mode;
means for triggering a refractory period in an atrial channel to prevent a retrograde P-wave, which may occur due to the PVC, from resetting an atrial escape interval (AEI), in response to detecting a PVC while the device is in AAI mode;
means for monitoring the atrial channel for a retrograde atrial event that may occur due to a PVC during a refractory period in the atrial channel that was triggered in response to detecting a PVC; and
means for terminating the refractory period in the atrial channel and beginning an antegrade conduction restoration interval (ACRI), in response to detecting a retrograde atrial event, wherein the ACRI is a programmed period that specifies how long to wait after the retrograde atrial event is detected before pacing the atrium.

20. The implantable cardiac device of claim 19, further comprising
   means for detecting the absence of atrioventricular (AV) conduction in response to two consecutive atrial events being detected in the atrial channel without an intervening ventricular event being detected in the ventricular channel, wherein the means for detecting the absence of AV conduction does not recognize a detected retrograde atrial event as an atrial event when determining whether there is an absence of AV conduction.

21. The implantable cardiac device of claim 20, further comprising:
   means for mode switching from AAI mode to DDD mode in response to detecting a persistent loss of AV conduction.

* * * * *